(12) United States Patent  (10) Patent No.: US 8,362,021 B2
Snutch et al.  (45) Date of Patent: Jan. 29, 2013

(54) METHOD FOR INCREASING THE BIOAVAILABILITY OF BENZHYDRYL PIPERAZINE CONTAINING COMPOUNDS

(75) Inventors: Terrance P. Snutch, Vancouver (CA); Dennis M. Fisher, San Francisco, CA (US)

(73) Assignee: Zalicus Pharmaceuticals Ltd., Vancouver, BC (CA)

( * ) Notice: Subject to any disclaimer, the term of this patent is extended or adjusted under 35 U.S.C. 154(b) by 811 days.

(21) Appl. No.: 12/300,076

(22) PCT Filed: May 4, 2007

(86) PCT No.: PCT/US2007/010846
§ 371 (c)(1),
(2), (4) Date: Mar. 19, 2009

(87) PCT Pub. No.: WO2007/133481
PCT Pub. Date: Nov. 22, 2007

(65) Prior Publication Data
US 2009/0312346 A1  Dec. 17, 2009

Related U.S. Application Data

(60) Provisional application No. 60/799,334, filed on May 11, 2006.

(51) Int. Cl.
*A61K 31/4965* (2006.01)

(52) U.S. Cl. .................................................. 514/255.01

(58) Field of Classification Search ............... 514/255.01
See application file for complete search history.

(56) References Cited

U.S. PATENT DOCUMENTS 3,288,795 A 11/1966 Irikura et al.
(Continued)

OTHER PUBLICATIONS

Schmidt and Dalhoff, Drugs, 2002;62(10):1481-1502.*

*Primary Examiner* — San-Ming Hui
(74) *Attorney, Agent, or Firm* — Clark & Elbing LLP

(57) ABSTRACT

A method of increasing the bioavailability of a compound of formula 1 by orally administering to a patient a compound of formula 1, or a pharmaceutically acceptable salt thereof, with food:

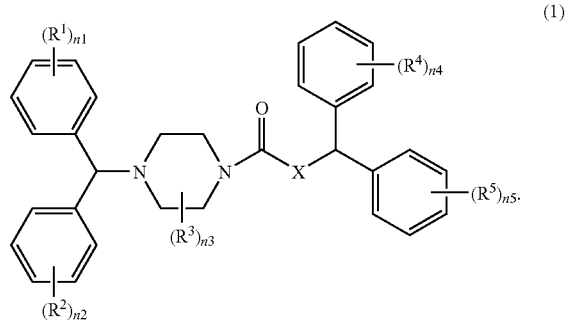

(1)

23 Claims, 4 Drawing Sheets

U.S. PATENT DOCUMENTS

| | | | |
|---|---|---|---|
| 3,445,464 A | 5/1969 | Jucker et al. | |
| 3,531,480 A | 9/1970 | Jucker et al. | |
| 4,188,485 A | 2/1980 | Kukla | |
| 4,411,904 A | 10/1983 | Pattison | |
| 4,751,230 A | 6/1988 | Laviella et al. | |
| 4,766,116 A | 8/1988 | Tatsuoka et al. | |
| 4,766,125 A | 8/1988 | Van Daele | |
| 4,782,071 A | 11/1988 | Butler et al. | |
| 4,883,797 A | 11/1989 | Foguet et al. | |
| 4,918,073 A | 4/1990 | Ruger et al. | |
| 5,292,726 A | 3/1994 | Ashton et al. | |
| 5,344,830 A | 9/1994 | Mills et al. | |
| 5,386,025 A | 1/1995 | Jay et al. | |
| 5,391,552 A | 2/1995 | Inazu et al. | |
| 5,428,038 A | 6/1995 | Chatterjee et al. | |
| 5,623,051 A | 4/1997 | Catterall et al. | |
| 5,646,149 A | 7/1997 | Hellberg et al. | |
| 5,703,071 A | 12/1997 | Iton et al. | |
| 5,866,574 A | 2/1999 | Okamura et al. | |
| 6,011,035 A | 1/2000 | Snutch et al. | |
| 6,090,631 A | 7/2000 | Catterall et al. | |
| 6,218,538 B1 | 4/2001 | Downs et al. | |
| 6,251,918 B1 | 6/2001 | Hu et al. | |
| 6,267,945 B1 | 7/2001 | Zamponi | |
| 6,294,533 B1 | 9/2001 | Snutch et al. | |
| 6,310,058 B1 | 10/2001 | Miller et al. | |
| 6,310,059 B1 | 10/2001 | Snutch | |
| 6,323,243 B1 | 11/2001 | Rafferty et al. | |
| 6,362,174 B1 | 3/2002 | Rafferty et al. | |
| 6,387,897 B1 | 5/2002 | Snutch | |
| 6,458,781 B1 | 10/2002 | Connor et al. | |
| 6,492,375 B2 | 12/2002 | Snutch | |
| 6,605,608 B1 | 8/2003 | Seko et al. | |
| 6,610,717 B2 | 8/2003 | Nakajo et al. | |
| 6,617,322 B2 | 9/2003 | Snutch | |
| 6,815,447 B2 | 11/2004 | Chaudhari et al. | |
| 6,841,680 B2 | 1/2005 | Chapdelaine et al. | |
| 6,943,168 B2 | 9/2005 | Snutch et al. | |
| 6,949,554 B2 | 9/2005 | Snutch et al. | |
| 6,951,860 B2 | 10/2005 | Mehanna et al. | |
| 6,951,862 B2 * | 10/2005 | Snutch et al. | 514/255.01 |
| 7,064,128 B2 | 6/2006 | Snutch et al. | |
| 7,186,726 B2 | 3/2007 | Snutch et al. | |
| 7,666,865 B2 | 2/2010 | Snutch et al. | |
| 2001/0029258 A1 | 10/2001 | Snutch | |
| 2003/0045530 A1 | 3/2003 | Snutch | |
| 2003/0199523 A1 | 10/2003 | Snutch | |
| 2004/0005359 A1 | 1/2004 | Cheng et al. | |
| 2004/0034035 A1 | 2/2004 | Snutch et al. | |
| 2004/0044004 A1 | 3/2004 | Snutch et al. | |
| 2004/0147529 A1 | 7/2004 | Snutch et al. | |
| 2004/0180323 A1 | 9/2004 | Belardetti et al. | |
| 2004/0192703 A1 | 9/2004 | Snutch et al. | |
| 2004/0209872 A1 | 10/2004 | Snutch et al. | |
| 2004/0266784 A1 | 12/2004 | Snutch et al. | |
| 2005/0014748 A1 | 1/2005 | Pajouhesh et al. | |
| 2005/0227999 A1 | 10/2005 | Pajouhesh et al. | |
| 2006/0084660 A1 | 4/2006 | Snutch et al. | |
| 2008/0227823 A1 | 9/2008 | Pajouhesh et al. | |
| 2008/0280900 A1 | 11/2008 | Pajouhesh et al. | |
| 2009/0012010 A1 | 1/2009 | Galemmo, Jr. et al. | |
| 2009/0221603 A1 | 9/2009 | Pajouhesh et al. | |
| 2009/0270338 A1 | 10/2009 | Galemmo, Jr. et al. | |
| 2009/0270394 A1 | 10/2009 | Pajouhesh et al. | |
| 2009/0270413 A1 | 10/2009 | Galemmo, Jr. et al. | |
| 2009/0286806 A1 | 11/2009 | Pajouhesh et al. | |
| 2009/0298834 A1 | 12/2009 | Pajouhesh et al. | |
| 2009/0298883 A1 | 12/2009 | Pajouhesh et al. | |
| 2010/0029681 A1 | 2/2010 | Pajouhesh et al. | |
| 2010/0105682 A1 | 4/2010 | Pajouhesh et al. | |
| 2010/0168103 A1 | 7/2010 | Pajouhesh et al. | |

* cited by examiner

METHOD FOR INCREASING THE BIOAVAILABILITY OF BENZHYDRYL PIPERAZINE CONTAINING COMPOUNDS

This application claims priority to U.S. Provisional Application Ser. No. 60/799,334, filed May 11, 2006, hereby incorporated by reference.

TECHNICAL FIELD

The invention relates to methods for increasing the bioavailability of a series of medicinal agents, namely benzhydryl piperazine containing compounds, useful in modulating N-type calcium channels.

BACKGROUND OF THE INVENTION

The entry of calcium into cells through voltage-gated calcium channels mediates a wide variety of cellular and physiological responses, including excitation-contraction coupling, hormone secretion and gene expression (Miller, R. J., *Science* (1987) 235:46-52; Augustine, G. J. et al., *Annu Rev Neurosci* (1987) 10: 633-693). In neurons, calcium channels directly affect membrane potential and contribute to electrical properties such as excitability, repetitive firing patterns and pacemaker activity. Calcium entry further affects neuronal functions by directly regulating calcium-dependent ion channels and modulating the activity of calcium-dependent enzymes such as protein kinase C and calmodulin-dependent protein kinase II. An increase in calcium concentration at the presynaptic nerve terminal triggers the release of neurotransmitter and calcium channels, which also affects neurite outgrowth and growth cone migration in developing neurons.

Calcium channels mediate a variety of normal physiological functions, and are also implicated in a number of human disorders. Examples of calcium-mediated human disorders include but are not limited to congenital migraine, cerebellar ataxia, angina, epilepsy, hypertension, ischemia, and some arrhythmias. The clinical treatment of some of these disorders has been aided by the development of therapeutic calcium channel antagonists (e.g., dihydropyridines, phenylalkyl amines, and benzothiazapines all target L-type calcium channels) (Janis, R. J. & Triggle, D. J., In Calcium Channels: Their Properties, Functions, Regulation and Clinical Relevance (1991) CRC Press, London).

Native calcium channels have been classified by their electrophysiological and pharmacological properties into T-, L-, N-, P/Q- and R-types (reviewed in Catterall, W., *Annu Rev Cell Dev Biol* (2000) 16: 521-555; Huguenard, J. R., *Annu Rev Physiol* (1996) 58: 329-348). T-type (or low voltage-activated) channels describe a broad class of molecules that transiently activate at negative potentials and are highly sensitive to changes in resting potential.

The L-, N- and P/Q-type channels activate at more positive potentials (high voltage-activated) and display diverse kinetics and voltage-dependent properties (Catterall (2000) supra; Huguenard (1996) supra). L-type channels can be distinguished by their sensitivity to several classes of small organic molecules used therapeutically, including dihydropyridines (DHP's), phenylalkylamines and benzothiazepines. In contrast, N-type and P/Q-type channels are high affinity targets for certain peptide toxins produced by venous spiders and marine snails: N-type channels are blocked by the ω-conopeptides ω-conotoxin GVIA (ω-CTx-GVIA) isolated from *Conus geographus* and ω-conotoxin MVIIA (ω-CTx-MVIIA) isolated from *Conus magus*, while P/Q-type channels are resistant to ω-CTx-MVIIA but are sensitive to the funnel web spider peptide, ω-agatoxin IVA (ω-Aga-IVA). R-type calcium channels are sensitive to block by the tarantula toxin, SNX-482.

Neuronal high voltage-activated calcium channels are composed of a large (>200 kDa) pore-forming $\alpha_1$ subunit that is the target of identified pharmacological agents, a cytoplasmically localized ~50-70 kDa $\beta$ subunit that tightly binds the $\alpha_1$ subunit and modulates channel biophysical properties, and an ~170 kDa $\alpha_2\delta$ subunit (reviewed by Stea, et al., *Proc Natl Acad Sci USA* (1994) 91:10576-10580; Catterall (2000) supra). At the molecular level, nine different $\alpha_1$ subunit genes expressed in the nervous system have been identified and shown to encode all of the major classes of native calcium currents.

Calcium channels have been shown to mediate the development and maintenance of the neuronal sensitization processes associated with neuropathic pain, and provide attractive targets for the development of analgesic drugs (reviewed in Vanegas, H. & Schaible, H-G., *Pain* (2000) 85: 9-18). All of the high-threshold Ca channel types are expressed in the spinal cord, and the contributions of L-, N and P/Q-types in acute nociception are currently being investigated. In contrast, examination of the functional roles of these channels in more chronic pain conditions strongly indicates a pathophysiological role for the N-type channel (reviewed in Vanegas & Schaible (2000) supra).

A considerable amount of effort has been undertaken by industry to develop an orally available N-type calcium channel antagonist. A series of potent N-type calcium channel antagonists have been disclosed in U.S. Pat. Nos. 6,294,533; 6,387,897; 6,951,862; and 6,949,554 and U.S. application Ser. Nos. 11/214,218 and 11/215,064.

While previous studies have demonstrated the ability of such compounds to block N-type calcium channels, there have not been any pharmacokinetic studies to evaluate the oral bioavailability of the compounds. There thus remains a need to better understand the pharmacokinetics and to correct any issues that may arise from such an understanding.

All patents, patent applications and publications disclosed herein are hereby incorporated by reference in their entirety.

SUMMARY OF THE INVENTION

A subject of the invention is the unexpected finding that administration of compounds of formula 1 with food markedly increases their extent of absorption when administered orally in human subjects. In particular, an aspect of the invention is a method of increasing the oral bioavailability of such compounds to a patient receiving treatment to modulate N-type calcium channels comprising administering to the patient a compound of formula 1 or a pharmaceutically acceptable salt thereof, optionally in a pharmaceutical composition, with food. Formula 1 is as follows:

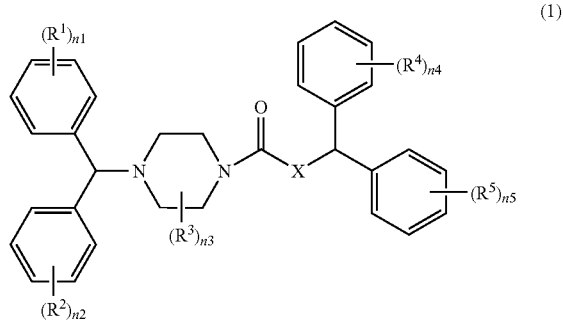

(1)

wherein X is C or N; $R^1$-$R^5$ are independently selected from $C_{1-6}$ alkyl, halo, $CF_3$, $OCF_3$, $NO_2$, $NR_2$, OR, SR, COR, COOR, $CONR_2$, NROCR or OOCR where R is H or $C_{1-4}$ alkyl, or any two substituents on the same ring may, along with the atoms to which they are joined, form a 5-7 membered ring, preferably wherein 0, 1, 2 or 3 of the atoms forming the ring are independently selected from O, S and N atoms, with the remainder of the atoms on the ring being carbon; $n^1$, $n^2$, $n^4$ and $n^5$ are independently 0-5, and $n^3$ is 0-4. As used herein, the term "alkyl" includes straight-chain, branched-chain and cyclic monovalent groups, containing only C and H. Preferred examples of alkyl groups for $R^1$-$R^5$ include methyl, ethyl, isobutyl, cylcohexyl, and t-butyl. The term "halo" includes any halogen atom (preferably Cl, F, Br or I) and more preferably Cl or F.

Specific embodiments of formula 1 include:
1-(3,3-diphenylpropionyl)-4-benzhydryl piperazine;
3,3-diphenyl-1-{4-[phenyl-(3-trifluoromethyl-phenyl)-methyl]-piperazin-1-yl}-propan-1-one;
1-{4-[(4-methoxy-phenyl)-(4-trifluoromethyl-phenyl)-methyl]-piperazin-1-yl}-3,3-diphenyl-propan-1-one;
1-{4-[3,5-di-tert-butyl-4-hydroxy-phenyl)-phenyl-methyl] piperazin-1-yl}-3,3-diphenyl-propan-1-one;
4-benzhydryl-1-(3,3-diphenyl-propionyl)-piperazine-2-carboxylic acid ethyl ester;
1-{4-[(4-chloro-phenyl)-phenyl-methyl]-piperazine-1-yl}-3,3-diphenyl-propan-1-one;
4-benzhydryl-1-(3,3-diphenyl-propionyl)-piperazine-2-carboxylic acid;
1-{4-[4-tert-butyl-phenyl)-phenyl-methyl]-piperazin-1-yl}-3,3-diphenyl-propan-1-one;
4-Benzhydryl-piperazine-1-carboxylic acid benzhydryl-amide;
4-[(4-Chloro-phenyl)-phenyl-methyl]-piperazine-1-carboxylic acid benzhydryl-amide;
4-[(3-Chloro-phenyl)-phenyl-methyl]-piperazine-1-carboxylic acid benzhydryl-amide;
4-[(2-Chloro-phenyl)-phenyl-methyl]-piperazine-1-carboxylic acid benzhydryl-amide; and
4-[(2,3-Dichloro-phenyl)-phenyl-methyl]-piperazine-1-carboxylic acid benzhydryl-amide.

In certain embodiments, the term "with food" means that a compound of formula 1 is administered at the same time or at substantially the same time as consuming food. For example, administration of a compound of formula 1 may occur between 30 minutes prior to consuming food and 2 hours after consumption. More preferably, administration of a compound of formula 1 may occur immediately after consuming food to one hour after consumption. Even more preferably, administration of a compound of formula 1 may occur immediately after consuming food to one half hour after consumption.

In certain embodiments, the term "with food" may comprise administering a compound of formula 1 with a normal fat meal or a high fat meal. A "normal fat" meal may comprise, for example, between 15 and 30% fat on a calorie basis, and more preferably between 15 and 25% fat on a calorie basis. A "high fat" meal may comprise, for example, between 45 and 65% fat on a calorie basis, and more preferably between 50 and 60% fat on a calorie basis.

Bioavailability of compounds of formula 1 may be significantly increased when administered with food or at substantially the same time as consuming food.

The compound of formula 1 is preferably provided in a therapeutically effective amount, which may be, for example, 25 to 1600 mg, more preferably 100 to 800 mg, and even more preferably 200-400 mg. In an embodiment, a pharmaceutical composition comprising a compound of formula 1 comprises a capsule, for example in unit dosage form.

In preferred embodiments, the treatment to modulate N-type calcium channels is a treatment for pain and more preferably, chronic pain.

The invention may further comprise informing the patient, preferably via printed materials, that the administration of a therapeutically effective amount of a compound of formula 1 with food results in an increase in the bioavailability of such a compound, as compared to administration without food. For example, the informing step may be via printed materials advising that administration with food results in an increase in the bioavailability of a compound of formula 1, and/or the patient may be instructed via printed materials to administer a compound of formula 1 with food.

The term "without food" may mean, for example, that the patient has not consumed any food for at least one hour, and more preferably for at least two hours, before administration of such a compound, and for at least 30 minutes after administration of such compound.

The compound of formula 1 may be provided in a container associated with printed materials advising that administration with food results in an increase in the bioavailability of the compound, as compared to administration without food, and/or instructing the patient to administer the compound with food.

In another aspect of the present invention, a method of using compounds of formula 1 to modulate N-type calcium channels comprises:
(a) providing a patient with a therapeutically effective amount of compound of formula 1; and
(b) informing the patient that the compound of formula 1 should be administered with food.

In a more preferred embodiment, the informing step comprises informing the patient that the administration of a compound of formula 1 with food results in an increase in bioavailability of such a compound, as compared to administration without food.

In addition, the informing step may comprise providing written instructions advising the patient to administer a compound of formula 1 with food, and more preferably, the written instructions may be on a label provided with a compound of formula 1.

In yet another aspect of the present invention, a pharmaceutical kit comprises: at least one therapeutically effective dosage of a compound of formula 1; and written instructions to administer the compound of formula 1 with food.

BRIEF DESCRIPTION OF THE DRAWINGS

In FIG. 3a, subjects consumed a normal fat meal whereas in FIG. 3b, subjects consumed a high fat meal.

In FIG. 4a, subjects consumed a normal fat meal whereas in FIG. 4b, subjects consumed a high fat meal.

DETAILED DESCRIPTION OF THE PREFERRED EMBODIMENTS

Figure 1:
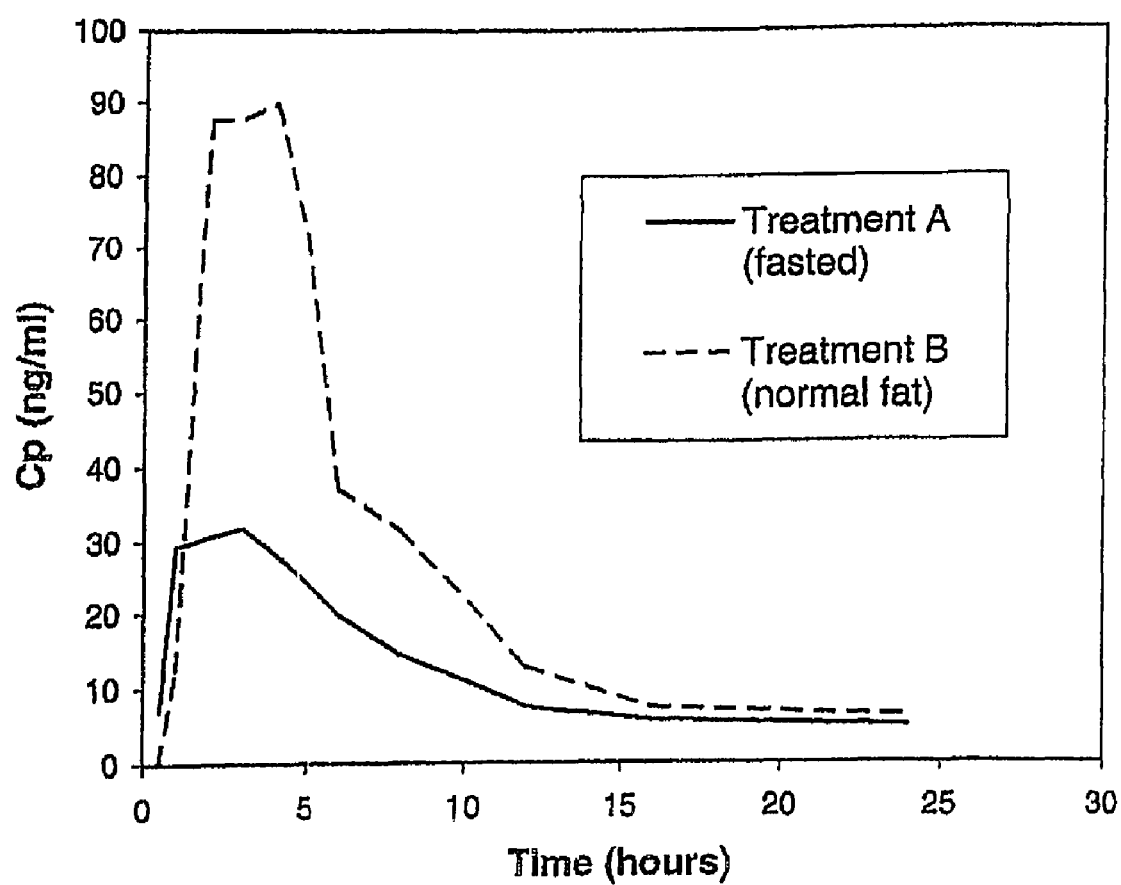
FIG. 1 is a plot of the mean plasma concentration of Compound No. 1 in nanograms per milliliter versus the time elapsed from administration of a 400 mg dosage. Two plots are shown for the 400 mg dosage form administered to subjects who have either fasted or consumed a normal fat diet.

Compounds of formula 1, as potent N-type calcium channel antagonists, may be used in the treatment of conditions associated with N-type calcium channels. Conditions where modulation of N-type calcium channels is desired include: chronic and/or acute pain; mood disorders such as anxiety, depression, and addiction; neurodegenerative disorders; gastrointestinal disorders such as inflammatory bowel disease and irritable bowel syndrome; genitourinary disorders such as urinary incontinence, interstitial colitis and sexual dysfunction; neuroprotection such as cerebral ischemia, stroke and traumatic brain injury; and metabolic disorders such as diabetes and obesity.

Acute pain includes but is not limited to nociceptive pain and post-operative pain. Chronic pain includes but is not limited to: peripheral neuropathic pain such as post-herpetic neuralgia, diabetic neuropathic pain, neuropathic cancer pain, failed back-surgery syndrome, trigeminal neuralgia, and phantom limb pain; central neuropathic pain such as multiple sclerosis related pain, Parkinson disease related pain, post-stroke pain, post-traumatic spinal cord injury pain, and pain in dementia; musculoskeletal pain such as osteoarthritic pain and fibromyalgia syndrome; inflammatory pain such as rheumatoid arthritis and endometriosis; headache such as migraine, cluster headache, tension headache syndrome, facial pain, headache caused by other diseases; visceral pain such as interstitial cystitis, irritable bowel syndrome and chronic pelvic pain syndrome; and mixed pain such as lower back pain, neck and shoulder pain, burning mouth syndrome and complex regional pain syndrome.

Anxiety includes but is not limited to the following conditions: generalized anxiety disorder, social anxiety disorder, panic disorder, obsessive-compulsive disorder, and post-traumatic stress syndrome. Addiction includes but is not limited to dependence, withdrawal and/or relapse of cocaine, opioid, alcohol and nicotine.

Neurodegenerative disorders include Parkinson's disease, Alzheimer's disease, multiple sclerosis, neuropathies, Huntington's disease and amyotrophic lateral sclerosis (ALS).

For greater certainty, in treating osteoarthritic pain, joint mobility will also improve as the underlying chronic pain is reduced. Thus, use of compounds of formula 1 to treat osteoarthritic pain inherently includes use of such compound to improve joint mobility in patients suffering from osteoarthritis.

Specific embodiments of compounds of formula 1 are provided below in Table 1.

TABLE 1

| Compound No. | Name | Structure |
|---|---|---|
| 1 | 1-(3,3-diphenylpropionyl)-4-benzhydryl piperazine | 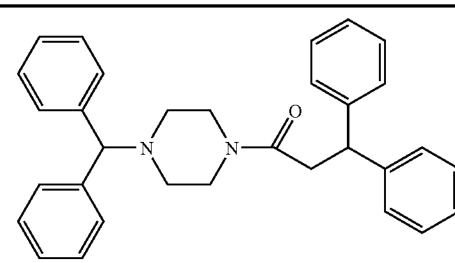 |
| 2 | 3,3-diphenyl-1-{4-[phenyl-(3-trifluoromethyl-phenyl)-methyl]-piperazin-1-yl}-propan-1-one | 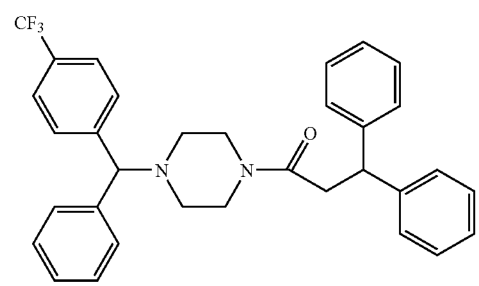 [SMILES: O=C(CC(c1ccccc1)c1ccccc1)N1CCN(C(c2ccccc2)c2ccc(C(F)(F)F)cc2)CC1] |
| 3 | 1-{4-[(4-methoxy-phenyl)-(4-trifluoromethyl-phenyl)-methyl]-piperazin-1-yl}-3,3-diphenyl-propan-1-one | 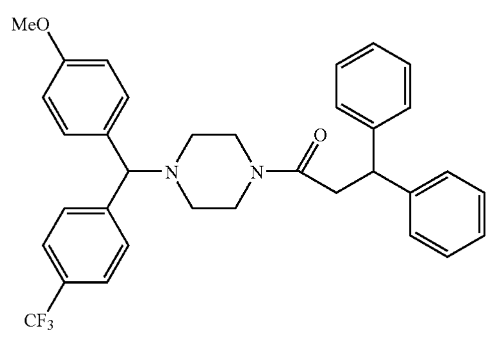 [SMILES: COc1ccc(C(c2ccc(C(F)(F)F)cc2)N2CCN(C(=O)CC(c3ccccc3)c3ccccc3)CC2)cc1] |

TABLE 1-continued

| Compound No. | Name | Structure |
|---|---|---|
| 4 | 1-{4-[3,5-di-tert-butyl-4-hydroxy-phenyl)-phenyl-methyl]piperazin-1-yl}-3,3-diphenyl-propan-1-one | 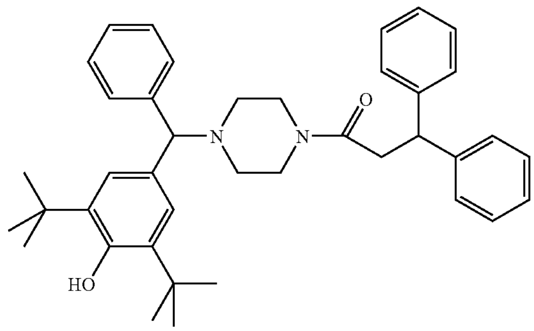 [SMILES: CC(C)(C)c1cc(C(c2ccccc2)N2CCN(C(=O)CC(c3ccccc3)c3ccccc3)CC2)cc(C(C)(C)C)c1O] |
| 5 | 4-benzhydryl-1-(3,3-diphenyl-propionyl)-piperazine-2-carboxylic acid ethyl ester | 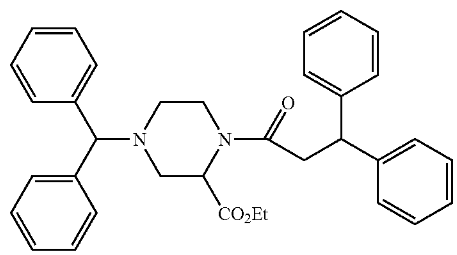 |
| 6 | 1-{4-[(4-chloro-phenyl-phenyl-methyl]-piperazine-1-yl}-3,3-diphenyl-propan-1-one | 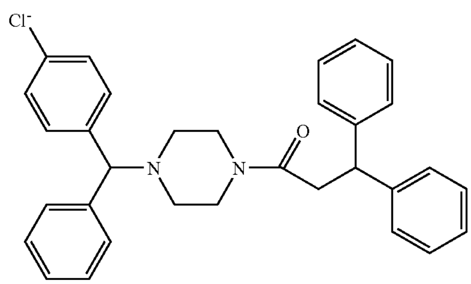 |
| 7 | 4-benzhydryl-1-(3,3-diphenyl-propionyl)-piperazine-2-carboxylic acid | 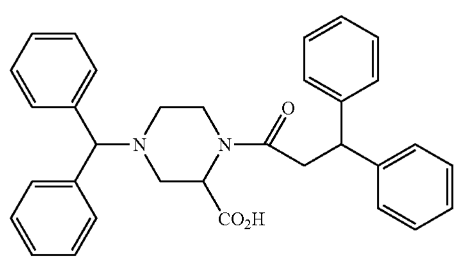 [SMILES: O=C(O)C1CN(C(c2ccccc2)c2ccccc2)CCN1C(=O)CC(c1ccccc1)c1ccccc1] |
| 8 | 1-{4-[-4-tert-butyl-phenyl)-phenyl-methyl]-piperazin-1-yl}-3,3-diphenyl-propan-1-one | 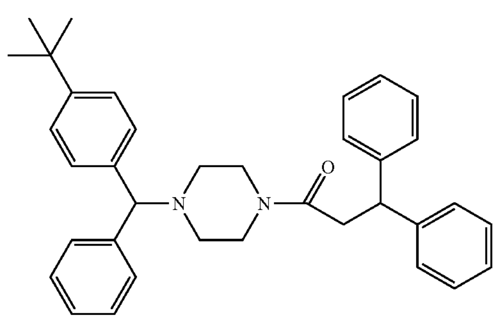 [SMILES: CC(C)(C)c1ccc(C(c2ccccc2)N2CCN(C(=O)CC(c3ccccc3)c3ccccc3)CC2)cc1] |

TABLE 1-continued

| Compound No. | Name | Structure |
|---|---|---|
| 9 | 4-Benzhydryl-piperazine-1-carboxylic acid benzhydryl-amide | 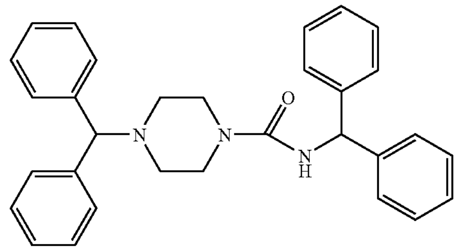 [SMILES: O=C(NC(c1ccccc1)c1ccccc1)N1CCN(C(c2ccccc2)c2ccccc2)CC1] |
| 10 | 4-[(4-Chloro-phenyl)-phenyl-methyl]-piperazine-1-carboxylic acid benzhydryl-amide | 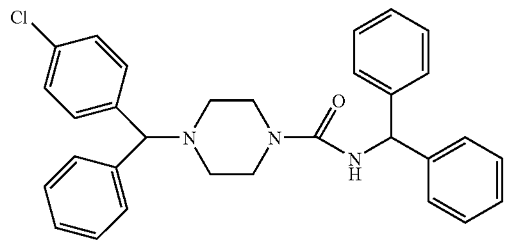 [SMILES: O=C(NC(c1ccccc1)c1ccccc1)N1CCN(C(c2ccccc2)c2ccc(Cl)cc2)CC1] |
| 11 | 4-[(3-Chloro-phenyl)-phenyl-methyl]-piperazine-1-carboxylic acid benzhydryl-amide | 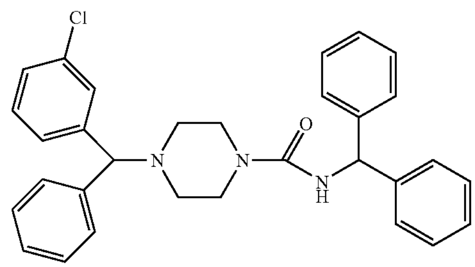 [SMILES: O=C(NC(c1ccccc1)c1ccccc1)N1CCN(C(c2ccccc2)c2cccc(Cl)c2)CC1] |
| 12 | 4-[(2-Chloro-phenyl)-phenyl-methyl]-piperazine-1-carboxylic acid benzhydryl-amide | 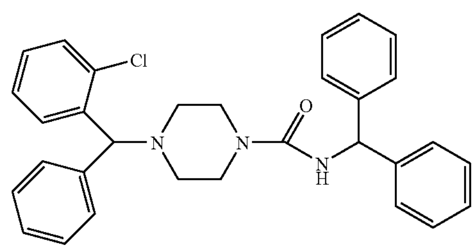 [SMILES: O=C(NC(c1ccccc1)c1ccccc1)N1CCN(C(c2ccccc2)c2ccccc2Cl)CC1] |
| 13 | 4-[(2,3-Dichloro-phenyl)-phenyl-methyl]-piperazine-1-carboxylic acid benzhydryl-amide | 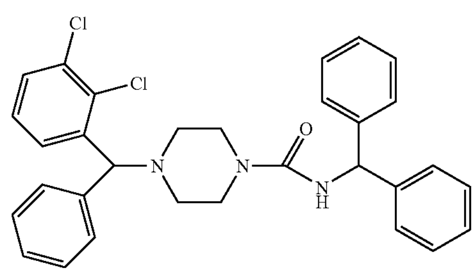 [SMILES: O=C(NC(c1ccccc1)c1ccccc1)N1CCN(C(c2ccccc2)c2cccc(Cl)c2Cl)CC1] |

For use as treatment of human and animal subjects, the compounds of the invention can be formulated as pharmaceutical or veterinary compositions. Depending on the subject to be treated, the mode of administration, and the type of treatment desired—e.g., prevention, prophylaxis, therapy; the compounds are formulated in ways consonant with these parameters. A summary of such techniques is found in *Remington's Pharmaceutical Sciences*, latest edition, Mack Publishing Co., Easton, Pa., incorporated herein by reference.

In general, for use in treatment, compounds of formula 1 may be used alone or in combination with other pharmaceuticals. An example of other potential pharmaceuticals to combine with compounds of formula 1 would include pharmaceuticals for the treatment of the same indication but having a different mechanism of action from N-type or T-type calcium channel blocking. For example, in the treatment of pain, compounds of formula 1 may be combined with another pain relief treatment such as an NSAID, or a compound which selectively inhibits COX-2, or an opioid, or an adjuvant analgesic such as an antidepressant or an anticonvulsant. Another example of a potential pharmaceutical to combine with compounds of formula 1 would include pharmaceuticals for the treatment of different yet associated or related symptoms or indications. Depending on the mode of administration, the compounds will be formulated into suitable compositions to permit facile delivery.

Formulations will generally include a diluent as well as, in some cases, adjuvants, buffers, preservatives and the like. Suitable forms for oral administration include syrups, capsules, and tablets, as is understood in the art, with capsules preferred. Various sustained release systems for drugs have also been devised. See, for example, U.S. Pat. No. 5,624,677.

For administration to animal or human subjects, the dosage of the compounds of the invention is typically 0.1 to 15 mg/kg, more preferably 3 to 5 mg/kg. However, dosage levels are highly dependent on the nature of the condition, drug efficacy, the condition of the patient, the judgment of the practitioner, and the frequency and mode of administration.

Oral administration of a pharmaceutical is often preferred due to the relative ease of administration. However, oral bioavailability may affect the suitability of a particular pharmaceutical for oral administration. One factor that has been observed in the oral bioavailability of some pharmaceuticals is a so-called "food effect" where the rate and/or absorption of the pharmaceutical increases when the patient has either a full or empty stomach.

A multitude of factors can influence the absorption and bioavailability of a particular drug, and absorption can be increased as well as decreased. Examples of such factors include pH-dependent solubility, site-specific intestinal permeation rate, instability to intestinal enzymes, susceptibility to first pass metabolism, and instability to colonic bacteria. Given the plethora of factors which can influence bioavailability, there usually is no way to predict in the absence of actual testing, whether a particular drug will exhibit a food effect. Some drugs have reduced absorption in the presence of food (cephalexin, cefaclor, metronidazole, aspirin, alclofenac, indoprofen, digoxin, cimetidine); some drugs are unaffected by food (ampicillin, erythromycin estolage, spiramycin, propylthiouracil, oxazepam, bendroflumethiazide); and some drugs exhibit increased absorption in the presence of food (erythromycin ethylsuccinate, nitrofurantoin, 8-methoxsalen, propranolol, metoprolol, dicoumarol, diazepam, hydrochlorothiazide).

The effect of food on absorption of a compound of formula 1 was identified in a study designed to compare the bioavailability of 25 mg to 1600 mg of a compound of formula 1 administered to healthy volunteers with and without food with the objective of ascertaining whether there was a food effect, if any. A single centre, single dose, open-label trial in healthy subjects was conducted. Study drug treatments were as follows:

Treatment A: Compound No. 1, in capsule form (25-400 mg) administered without food;

Treatment B: Compound No. 1, in capsule form (400-800 mg) administered with a normal fat meal;

Treatment C: Compound No. 1, in capsule form (400-1600 mg) administered with a high-fat meal.

In treatment A, subjects fasted overnight with water permitted up to one hour before dosing. One or more 25 mg or 100 mg capsules of Compound No. 1 were administered with 240 mL room temperature water. Subjects continued to fast for approximately 4 hours until lunch. All meals and snacks provided during the study were low fat and standardized. Additional water was allowed ad lib but there was no caffeine, smoking or alcohol and no vigorous exercise.

In treatments B and C, subjects consumed breakfast the day of the study. Breakfast commenced approximately 30 minutes prior to dosing with dosing occurring within 10 minutes after finishing the meal. One or more 25 mg or 100 mg capsules containing Compound No. 1 were administered to the subjects with 240 mL room temperature water. After dosing, subjects consumed no food until lunch and otherwise followed the same protocol as in treatment A.

In treatment B, a normal fat meal consisted of: toast with 1 pat of butter; a banana; 2% milk; apple juice; and Honey Nut Cheerios®. In treatment C, a high fat meal consisted of: 2 slices of buttered toast, 2 eggs fried in butter, 2 slices of bacon, 4 oz hash brown potatoes and 8 oz of whole milk. Table 2 provides a caloric breakdown of the two breakfast protocols.

TABLE 2

|  | Normal Fat Meal | High Fat Meal |
|---|---|---|
| Total calories | 501 | 1000 |
| Fat | 99 | 500-600 |
| Carbohydrate | 346 | 250 |
| Protein | 56 | 150 |

Subjects received one or two doses. There was a washout period of at least 14 days between study drug administrations in those subjects dosed more than once. Subjects who received a second dose received either a different formulation (e.g. 100 mg capsules vs. 25 mg capsules) or had a different fed status (e.g. fed vs. fasted). The actual dosing and sample times were recorded on a Case Report Form. At least 15 blood samples were collected during the period from pre-dose through 48 hours post-dose; in most subjects, additional samples were obtained at 60, 72, 120, 168 and 336 hours post-dose. Concentrations of Compound No. 1 were determined in plasma by BASi Northwest Laboratories Inc. (McMinnville, Oreg.) by LC-MS/MS. The lower limit of quantitation for Compound No. 1 was 0.05 ng/mL. Sample values below the lower limit of quantitation were reported as "<0.05 ng/mL".

A total of 60 subjects (29 males and 31 females) were enrolled and dosed. A mouth check was performed to verify that the subjects swallowed the dose. The actual time of dosing was recorded on a Case Report Form.

The drug substance, Compound No. 1 was dosed in capsule form as follows:

25 mg capsules: #1 white opaque hard gelatin shells containing Fast Flo lactose, surfactants, and disintegrants; batch nos. C0292A01, C0441A001.

100 mg capsules: HPMC capsules containing Fast Flo lactose, surfactants, and disintegrants; batch nos. C0519Z002, C0159AW002S Pharmacokinetic parameters were obtained using compartmental methods. Relative exposure was quantified through the term relative bioavailability. In that none of the subjects received an intravenous dose of Compound No. 1, absolute bioavailability could not be determined. Hence, relative bioavailability is referenced to the value obtained in subjects administered 100 mg of Compound No. 1 as 100 mg capsules following a normal fat meal (treatment B). There were no protocol deviations that confounded the pharmacokinetic analyses.

Statistical analyses were performed using NONMEM version 5. Study results were not corrected for drug potency. "Typical" values obtained in the pharmacokinetic analysis are reported in table 3. Relative bioavailability as a function of dose, capsule content, and meal is reported in table 4.

TABLE 3

Relative bioavailability of Compound No. 1 as a function of fasted/fed status, dose, and capsule content.

| | |
|---|---|
| Fasted (relative to normal-fat meal) | 0.682 |
| 25-mg capsules, (relative to 100-mg capsules) | 1.48 |
| High-fat meal, capsules (relative to normal-fat meal) | 5.60 |
| As function of dose (mg) (relative to 100-mg dose) | $1 - 0.363 \cdot \log10(Dose/100)$ |

*Computed as $100\% \cdot \sqrt{omega^2}$ where $omega^2$ = variance(eta); sixty-eight % of the population lies within this range of the typical value.

TABLE 4

Bioavailability of capsules as a function of dose, capsule content, and fed status derived from the "typical" values (Table 1). Values are expressed relative to the 100-mg dose administered with a normal-fat meal.

| | | | Meal | |
|---|---|---|---|---|
| Formulation | Dose (mg) | Fasted | Normal-fat | High-fat |
| 100-mg Capsules | 100 | 0.682 | 1.000 | 5.600 |
| | 200 | 0.607 | 0.891 | 4.988 |
| | 400 | 0.533 | 0.781 | 4.376 |
| | 800 | 0.458 | 0.672 | 3.764 |
| | 1600 | 0.384 | 0.563 | 3.152 |
| 25-mg Capsules | 25 | 1.230 | N.A.* | 10.10 |
| | 50 | 1.120 | | 9.19 |
| | 100 | 1.009 | | 8.29 |
| | 200 | 0.899 | | 7.38 |
| | 400 | 0.789 | | 6.48 |
| | 800 | 0.678 | | 5.57 |
| | 1600 | 0.568 | | 4.67 |

*No subjects were dosed with 25-mg capsules following a normal-fat meal.

Following oral administration, Compound No. 1 was absorbed rapidly when subjects were fasted (Tmax typically less than 2 hours with an absorption half-life ranging from 0.05-0.17 hours), but slower when subjects were fed a normal fat meal (Tmax 2-5 hours with an absorption half-life ranging from 0.5 to 1.6 hours) or a high fat meal (Tmax typically 4-5 hours with an absorption half-life of 0.8 to 2.8 hours). Compared to a normal fat meal, the high fat meal increased bioavailability of capsules 460%, while fasting decreased bioavailability 32%.

Figure 2:
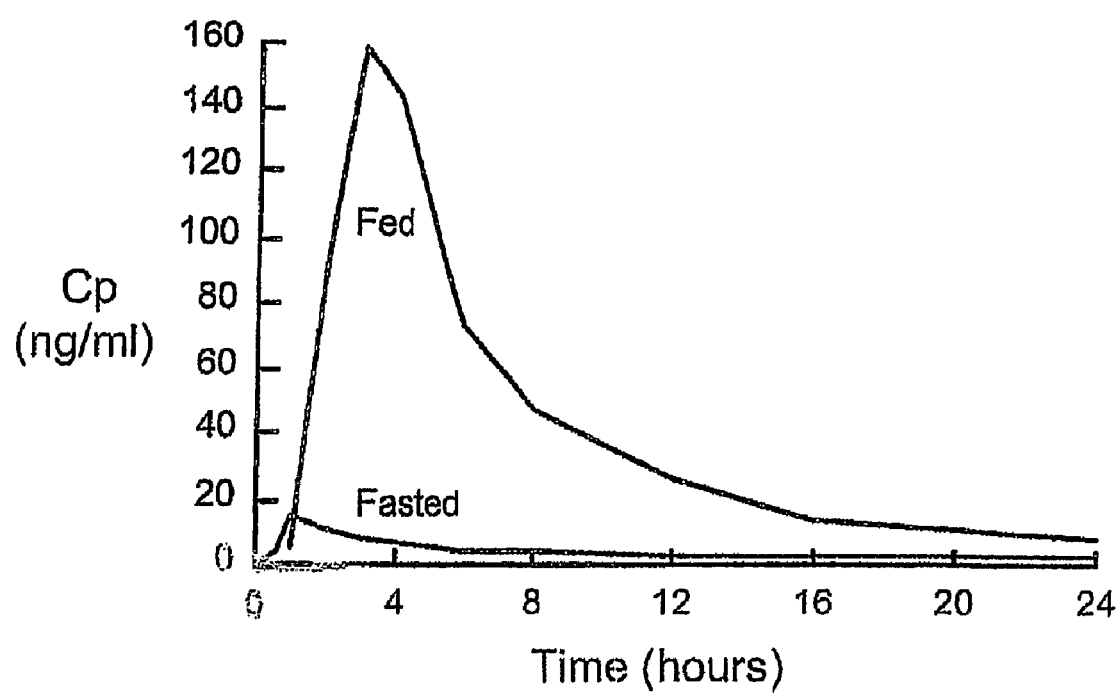
FIG. 2 is a plot of the mean plasma concentration of Compound No. 1 in nanograms per milliliter versus the time elapsed from administration of a 100 mg dosage. Two plots are shown for the 100 mg dosage form administered to subjects who have either fasted or consumed a high fat diet.

Representative results are shown in FIGS. 1-4. FIG. 1 is a plot of the mean plasma concentration of Compound No. 1 in nanograms per milliliter versus the time elapsed from administration of a 400 mg dosage with 100 mg capsules for the first 24 hours. Two plots are shown for the 400 mg dosage form administered to subjects who have either fasted (treatment A, solid line) or consumed a normal fat diet (treatment B, dashed line). The solid line represents the mean taken from four subjects sampled whereas the dashed line represents the mean taken from three subjects sampled. A significant increase in bioavailability is thus observed when Compound No. 1 is administered orally with food, as compared to without food. This difference is even more significant when comparing treatment A (fasted) with treatment C (high fat meal) as shown in FIG. 2.

FIG. 2 is a plot of the mean plasma concentration of Compound No. 1 in nanograms per milliliter versus the time elapsed from administration of a 100 mg dosage. Two plots are shown for the 100 mg dosage form administered to subjects who have either fasted (labeled as fasted) or consumed a high fat diet (labeled as fed).

Figure 3A:
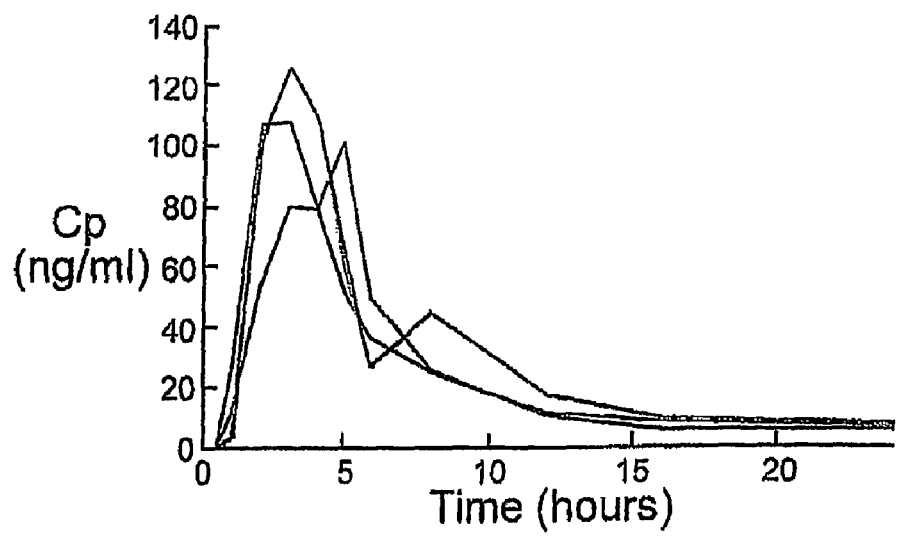
FIGS. 3a and 3b are plots of the individual plasma concentrations of Compound No. 1 in nanograms per milliliter versus the time elapsed from administration of a 400 mg dosage.
Figure 3B:
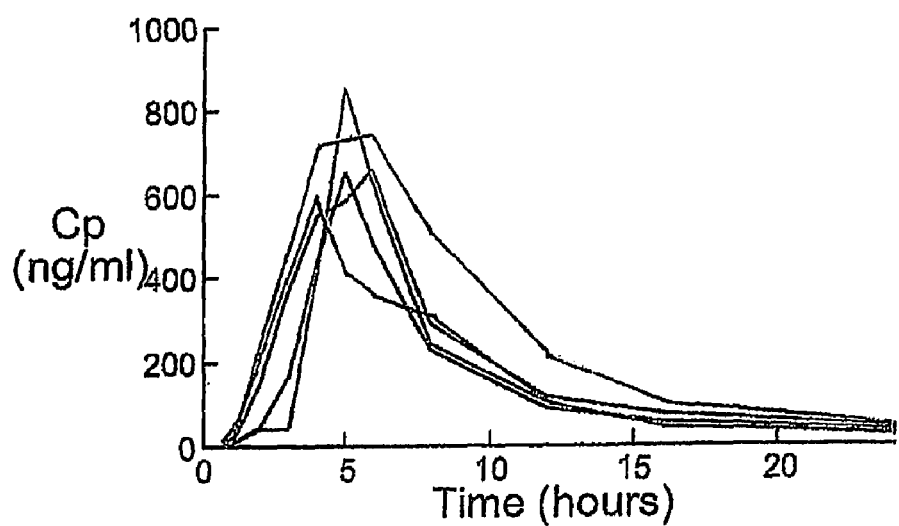
Figure 4A:
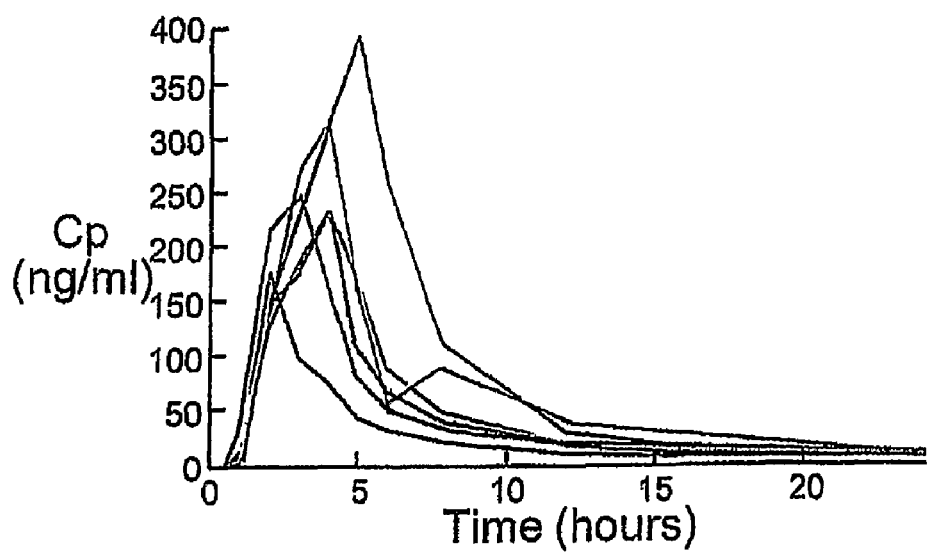
FIGS. 4a and 4b are plots of the individual plasma concentrations of Compound No. 1 in nanograms per milliliter versus the time elapsed from administration of a 800 mg dosage.
Figure 4B:
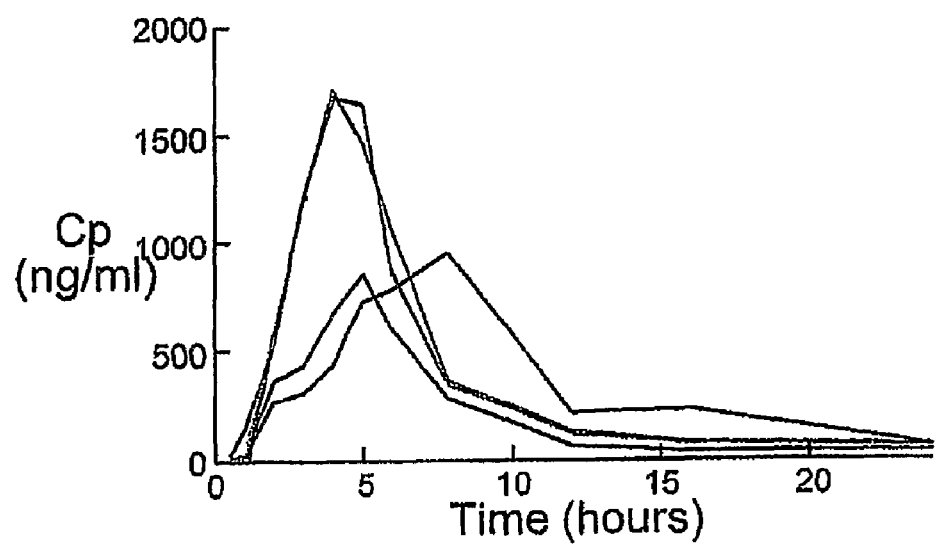

Increased bioavailability is also observed between treatments B (normal fat) and C (high fat) as shown in FIGS. 3 and 4. FIGS. 3a and 3b are plots of individual plasma concentrations of Compound No. 1 in nanograms per milliliter versus the time elapsed from administration of a 400 mg dosage. In FIG. 3a, subjects consumed a normal fat meal whereas in FIG. 3b, subjects consumed a high fat meal. Similarly, FIGS. 4a and 4b are plots of individual plasma concentrations of Compound No. 1 in nanograms per milliliter versus the time elapsed from administration of an 800 mg dosage. In FIG. 4a, subjects consumed a normal fat meal whereas in FIG. 4b, subjects consumed a high fat meal. FIGS. 3 and 4 both illustrate increased bioavailability of Compound No. 1 when meals of increasing fat content were consumed.

Naturally, a high fat meal may not be recommended for many individuals being treated with compounds of formula 1, particularly those being treated for chronic conditions. However, for some individuals, particularly those being treated for acute conditions, administration of compounds of formula 1 with a high fat meal may be justified. In any event, bioavailability of compounds of formula 1 is significantly increased when administered with food, including either a normal fat meal or a high fat meal.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

We claim:

1. A method of increasing the bioavailability of a compound of formula 1 in a patient receiving treatment to modulate N-type calcium channels, comprising orally administering to the patient a compound of formula 1, or a pharmaceutically acceptable salt thereof, with food, wherein the compound of formula 1 is:

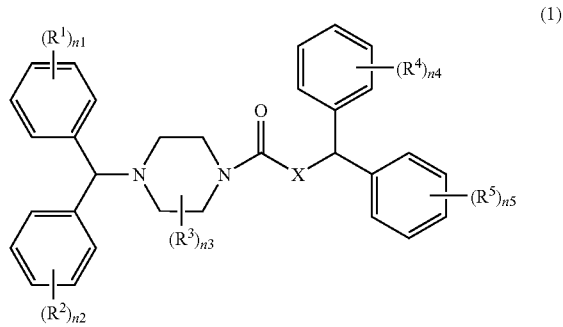

(1)

wherein

X is C or N;

$R^1$-$R^5$ are independently selected from $C_{1-6}$ alkyl, halo, $CF_3$, $OCF_3$, $NO_2$, $NR_2$, OR, SR, COR, COOR, $CONR_2$, NROCR or OOCR, wherein R is H or $C_{1-4}$ alkyl, or any two substituents on the same ring may, along with the atoms to which they are joined, form a 5-7 membered ring;

$n^1$, $n^2$, $n^4$ and $n^5$ are independently 0-5; and $n^3$ is 0-4.

2. The method of claim 1, wherein the compound is selected from the group consisting of:
 1-(3,3-diphenylpropionyl)-4-benzhydryl piperazine;
 3,3-diphenyl-1-{4-[phenyl-(3-trifluoromethyl-phenyl)-methyl]-piperazin-1-yl}-propan-1-one;
 1-{4-[(4-methoxy-phenyl)-(4-trifluoromethyl-phenyl)-methyl]-piperazin-1-yl}-3,3-diphenyl-propan-1-one;

1-{4-[3,5-di-tert-butyl-4-hydroxy-phenyl)-phenyl-methyl]-piperazin-1-yl}-3,3-diphenyl-propan-1-one;

4-benzhydryl-1-(3,3-diphenyl-propionyl)-piperazine-2-carboxylic acid ethyl ester;

1-{4-[(4-chloro-phenyl)-phenyl-methyl]-piperazine-1-yl}-3,3-diphenyl-propan-1-one;

4-benzhydryl-1-(3,3-diphenyl-propionyl)-piperazine-2-carboxylic acid;

1-{4-[4-tert-butyl-phenyl)-phenyl-methyl]-piperazin-1-yl}-3,3-diphenyl-propan-1-one;

4-Benzhydryl-piperazine-1-carboxylic acid benzhydryl-amide;

4-[(4-Chloro-phenyl)-phenyl-methyl]-piperazine-1-carboxylic acid benzhydryl-amide;

4-[(3-Chloro-phenyl)-phenyl-methyl]-piperazine-1-carboxylic acid benzhydryl-amide;

4-[(2-Chloro-phenyl)-phenyl-methyl]-piperazine-1-carboxylic acid benzhydryl-amide; and 4-[(2,3-Dichloro-phenyl)-phenyl-methyl]-piperazine-1-carboxylic acid amide, or a pharmaceutically acceptable salt thereof.

3. The method of claim 1, wherein the compound is 1-(3,3-diphenylpropionyl)-4-benzhydryl piperazine.

4. The method of claim 1, wherein the compound is administered in a therapeutically effective amount which is between 25 and 1600 mg.

5. The method of claim 1, wherein the compound is administered in a therapeutically effective amount which is between 100 and 800 mg.

6. The method of claim 1, wherein the compound is administered in a therapeutically effective amount which is between 200 and 400 mg.

7. The method of claim 1, wherein the compound is administered between 30 minutes prior to consuming food and 2 hours after consuming food.

8. The method of claim 1, wherein the compound is administered at substantially the same time as food is consumed.

9. The method of claim 1, wherein the compound is administered between immediately after consuming food and up to 1 hour after consuming food.

10. The method of claim 1, wherein the food comprises a normal fat meal.

11. The method of claim 1, wherein the food comprises a high fat meal.

12. The method of claim 1, wherein the compound is administered in a pharmaceutical composition.

13. The method of claim 12, wherein the pharmaceutical composition comprises a capsule.

14. The method of claim 1, wherein the patient is receiving treatment for pain.

15. The method of claim 1, wherein the patient is receiving treatment for chronic pain.

16. The method of claim 1, further comprising informing the patient that the administration of the compound with food results in an increase in the bioavailability of the compound, as compared to administration without food, and/or instructing the patient to administer the compound with food.

17. The method of claim 1, further comprising providing the compound in a container associated with printed materials informing the patient that administration of the compound with food results in an increase in the bioavailability of the compound, as compared to administration without food, and/or instructing the patient to administer the compound with food.

18. The method of claim 3, wherein the mean plasma concentration peaks within the first 5 hours after administration.

19. The method of claim 18, wherein the mean plasma concentration peaks within the first 4 hours after administration.

20. The method of claim 19, wherein the mean plasma concentration is between 40-160 ng/mL.

21. The method of claim 3, wherein the mean plasma concentration is at least 20 ng/mL for at least 12 hours after administration.

22. The method of claim 3, wherein the mean plasma concentration is at least 40 ng/mL for at least 8 hours after administration.

23. The method of claim 22, wherein the mean plasma concentration is at least 20 ng/mL after 12 hours post administration.

* * * * *

UNITED STATES PATENT AND TRADEMARK OFFICE
CERTIFICATE OF CORRECTION

PATENT NO.        : 8,362,021 B2
APPLICATION NO.   : 12/300076
DATED             : January 29, 2013
INVENTOR(S)       : Snutch et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 812 days.

Signed and Sealed this
Seventeenth Day of September, 2013

Teresa Stanek Rea
*Deputy Director of the United States Patent and Trademark Office*